United States Patent [19]

Casals-Stenzel et al.

[11] Patent Number: 4,622,319
[45] Date of Patent: Nov. 11, 1986

[54] METHODS OF USING PAF-ANTAGONISTIC DIAZEPINES

[75] Inventors: Jorge Casals-Stenzel, Mainz; Karl-Heinz Weber, Gau-Algesheim; Gerhard Walther, Bingen am Rhein; Albrecht Harreus; Gojko Muacevic, both of Ingelheim am Rhein, all of Fed. Rep. of Germany

[73] Assignee: Boehringer Ingelheim KG, Ingelheim am Rhein, Fed. Rep. of Germany

[21] Appl. No.: 782,631

[22] Filed: Oct. 1, 1985

[30] Foreign Application Priority Data

Oct. 1, 1984 [DE] Fed. Rep. of Germany ....... 3435972

[51] Int. Cl.$^4$ ............................................. A61K 31/55
[52] U.S. Cl. ..................................................... 514/220
[58] Field of Search ......................................... 514/220

Primary Examiner—Stanley J. Friedman
Attorney, Agent, or Firm—David E. Frankhouser; Charles J. Herron; Alan R. Stempel

[57] ABSTRACT

The invention discloses a method of treating an individual having a disorder responsive to PAF-antagonist activity by treating the individual with a compound of formula I or II

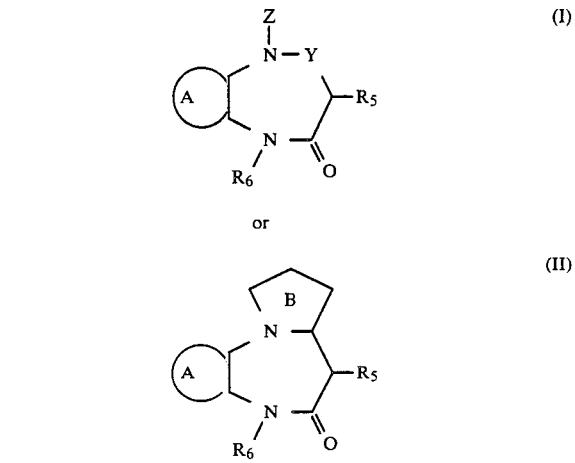

wherein A is an anellated and optionally substituted benzene or 5- or 6-membered heterocyclic ring; $R_5$ and Z are each independently hydrogen or an optionally substituted $C_1$-$C_8$ alkyl, alkenyl or alkynyl; $R_6$ is an optionally substituted phenyl, or is thienyl or is α-pyridyl; Y is CO, CS or $CH_2$; and nontoxic, pharmaceutically acceptable acid addition salts thereof.

13 Claims, No Drawings

METHODS OF USING PAF-ANTAGONISTIC DIAZEPINES

The invention relates to pharmaceutical compositions containing diazepines and having a PAF-antagonistic activity. Many of the diazepines are already known, while others are new.

PAF (platelet activating factor) is acetylglyceryl-ester-phosphorylcholine (AGEPC). This compound is known as a powerful lipid mediator which is released by animal and human pro-inflammatory cells. Among these cells are found mainly basophilic and neutrophilic granulocytes, macrophages (from the blood or tissues) and thrombocytes which participate in inflammatory reactions.

In pharmacological experiments, PAF shows the following activities:

(a) bronchoconstriction which is about a hundred times more powerful than that of histamine;
(b) a lowering of blood pressure, which is presumably due to direct peripheral vasodilation;
(c) triggering of thrombocyte aggregation (demonstrated in vitro and in vivo);
(d) pro-inflammatory activity by adhesion and aggregation of neutrophils, followed by the release of lysosomal enzymes and activation of arachidonic acid metabolism (tested in vitro).

These experimentally demonstrable activities of PAF indicate, directly or indirectly, possible functions of this mediator in anaphylaxis, in the pathophysiology of bronchial asthma and in inflammation.

PAF antagonists are needed to clarify further pathophysiological functions of this mediator in humans and animals and for treating pathological conditions and diseases in which PAF is involved. Examples of indications of a PAF antagonist include inflammatory processes of the tracheobronchial tree, acute and chronic bronchitis, bronchial asthma, anaphylactic conditions, allergies and inflammation in the mucous membranes and skin.

Substances with a PAF-antagonistic activity are already known, for example substances whose structures resemble that of PAF (European Patent Application No. 94586; U.S. Pat. No. 4,329,302; Japanese Patent Applications Nos. 57165394, 58035116, 58154512) and 11-oxopyridoquinazolines (European Patent Application No. 94080). Moreover, compounds from the following ranges of indications have been investigated for a PAF-antagonistic activity: calcium antagonists, anti-allergic agents, anti-inflammatory agents and α-adrenergic agents.

Surprisingly, it has now been found that numerous substances from a group of compounds which has hitherto not been taken into consideration, namely the diazepines, have a powerful PAF-antagonistic activity.

In the last twenty years, thousands of molecular variants of diazepines have been synthesized and tested pharmacologically, biochemically and in some cases clinically as well. The majority of diazepines, particularly those of the 1,4 series, have anticonvulsive, anxiolytic, muscle-relaxant and, to a greater or lesser extent, sedative activities (S. Garrantini et al. "The Benzodiazepines", Raven Press, New York 1973). Of the variety of structures, there are a few exceptions whose activity profile shows a different picture. Thus, diazepines which are effective against bilharzia (Drugs of the future 5, 43 (1980)) and against high blood pressure (European Patent Application No. 87850) are known. Other diazepines were found to have analgesic properties (D. Romer et al. Nature 298, 759 (1982)) and an affinity with the dopamine receptor (Ruhland and Liepmann, C.I.N.P. Congress, Nuremberg (1983)). The PAF-antagonistic activity of diazepines was never considered.

The invention therefore relates to a method of treating an individual having a disorder responsive to PAF-antagonist activity, which method comprises treating said individual with one or more compounds of formula:

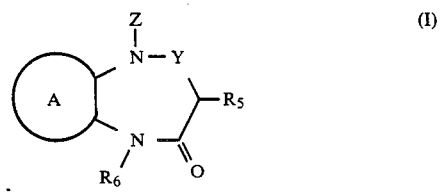

(I)

or

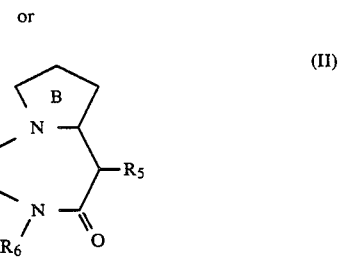

(II)

In these formulae
A is an anellated ring of formula

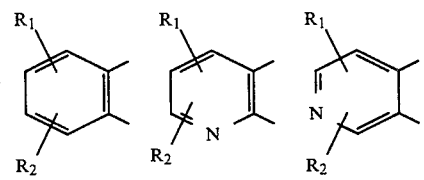

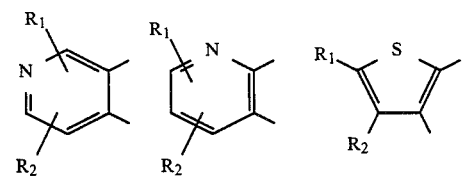

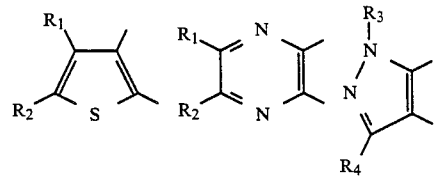

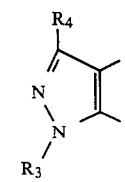

B is an anellated ring of formula

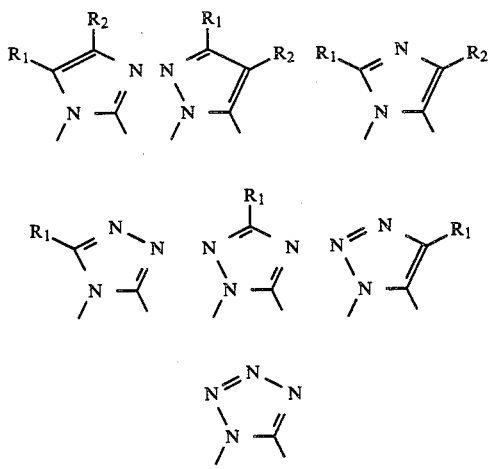

$R_1$ and $R_2$ are each independently hydrogen, a $C_1$-$C_8$ straight-chained or branched alkyl, alkenyl or alkynyl optionally mono- or polysubstituted by halogen, hydroxy, alkoxy, alkylmercapto, amino, alkylamino, dialkylamino, alkylcarbonyl, alkyloxycarbonyl or an acid amide group; cycloalkyl; a saturated carbocyclic or heterocyclic ring condensed on, which may contain oxygen, sulphur or nitrogen as a heteroatom while the nitrogen-containing ring may carry an alkyl group at the nitrogen atom; halogen, trifluoromethyl, nitro, cyano, optionally substituted amino, alkylmercapto, alkylcarbonyl, alkoxy, alkyloxycarbonyl or an acid amide group;

$R_3$, $R_4$, $R_5$ and Z are each independently hydrogen, a $C_1$-$C_8$ straight-chained or branched alkyl, alkenyl or alkynyl optionally mono- or polysubstituted by halogen, hydroxy, alkoxy, alkylmercapto, amino, alkylamino, dialkylamino, alkylcarbonyl, alkyloxycarbonyl or an acid amide group;

$R_6$ is phenyl, which can optionally be substituted, preferably in the 2 position, by methyl, methoxy, halogen, nitro or trifluoromethyl, or $R_6$ can be thienyl or α-pyridyl;

Y is <CO, <CS or <CH$_2$; and non-toxic, pharmaceutically acceptable acid addition salts thereof.

Unless otherwise stated Hal is fluorine, chlorine, bromine or iodine; and alkyl is a $C_1$-$C_8$ straight-chained or branched alkyl. The term "acid amide group" means an aminocarbonyl group which is mono- or disubstituted by alkyl at the nitrogen; this definition also covers an aminocarbonyl group which is closed, incorporating the nitrogen atom to form a five or six membered ring, while the hetero ring can optionally contain as a further heteroatom an oxygen, nitrogen or sulphur atom, and any nitrogen atom additionally present in the ring can carry an alkyl group as substituent.

The above compound of formula I and II are known or can be obtained by known methods such as those described, for example, in Jeffrey W. H. Watthey et al "Heterocyclic Compounds" Volume 43 (1984), "Azepines" Part 2, published by John Wiley & Sons Inc. and L. H. Sternbach "Progress in Drug Research" Volume 22 (1978) page 229–263, Birkhauser Verlag Basel. Compounds of formula I and II. which contain a carboxylic acid function may be obtained as water-soluble alkali or alkaline earth metal salts.

PHARMACOLOGICAL TEST RESULTS

The PAF-antagonistic activity of compounds of formulae I and II was investigated in terms of the inhibition of blood platelet aggregation in vitro and the antagonizing of PAF-induced bronchoconstriction in anesthetized guinea pigs.

1. Inhibition of blood platelet aggregation in vitro

The PAF-induced aggregation of human thrombocytes in vitro is used to determine PAF-antagonistic activity. To obtain thrombocyte-rich plasma (TRP), blood is taken from an uncongested vein using a plastic syringe containing 3.8% sodium citrate solution. The ratio of sodium citrate solution to blood is 1:9. After careful mixing the citrate blood is centrifuged for 20 minutes at 150 g (1200 rpm). The thrombocyte aggregation is measured using the method devised by Born and Cross (G. V. R. Born and M. J. Cross, J. Physiol. 168, 178 (1963)), by adding an aggregation initiator (PAF) to the TRP with constant stirring.

The test substance is added 2 to 3 minutes before aggregation is initiated in a volume of 10 μl. Either distilled water, ethanol and/or dimethylsulphoxide (each in suitable concentrations) can be used as solvent. Control mixtures contain corresponding volumes of these solvents. After the initial absorption has been recorded (2 to 3 minutes) aggregation is induced with PAF ($5 \times 10^{-8}$M).

The maximum of the first aggregation wave is used to assess the effects of the substance. The PAF-induced maximum absorption rate ($\hat{=}$maximum aggregation$\times 100\%$) is tested at the same time in a parallel mixture (=control mixture in one of the channels of the two-channel aggregometer) as each test mixture (second channel) and is used as a 100% value.

The aggregation value attained under the effect of the test substance is given as a percentage of the control value, i.e. less than 100% in the case of an inhibition of aggregation and over 100% in the case of an increase.

Each test substance is investigated at concentrations of from $10^{-3}$ to $10^{-8}$M with a random sampling of n=4 with regard to an inhibitory effect on the PAF-induced thrombocyte aggregation. Then a concentration-activity curve is drawn up using 3 concentrations and the IC$_{50}$ is determined (concentration giving a 50% inhibition of aggregation).

2. Antagonism of PAF-induced bronchoconstriction in anesthetized guinea pigs

Spontaneously breathing male guinea pigs weighing from 300 to 450 g are pretreated orally with the test substance or a control vehicle 1 hour before the intravenous infusion with PAF (30 mg/kg$\times$min). The test animals are then anesthetized by intraperitoneal route with 2 mg/kg of urethane, after which the jugular vein, carotid artery and trachea are cannulated. In the control animals the infusion of PAF induces a powerful and long-lasting bronchoconstriction which is measured in terms of the volume of the respiratory tract, compliance and resistance, and also a lowering of blood pressure. After about 7 to 8 minutes death occurs. These effects on respiration and blood pressure and the onset of death are prevented by the PAF antagonists described. Suitble dosages include from about 1 to about 50 mg/kg p.o. and 0.1 to 1.0 mg/kg i.v.

The following Table gives the IC$_{50}$ of a number of compounds of formulae I and II:

Compounds of formula:

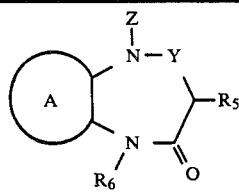
| No. | A | Z | R5 | Y | R6 | PAF-Antag. IC50; [μMol] | Mp. °C. |
|---|---|---|---|---|---|---|---|
| 1 Clobazam | 4-Cl-phenyl | CH3 | H | CO | phenyl | 250 | 170–172 |
| 2 Triflubazam | 4-CF3-phenyl | CH3 | H | CO | phenyl | 200 | 203–205 |
| 3 | 4-Br-phenyl | H | H | CO | phenyl | 470 | 302–304 |
| 4 | 4-Cl-phenyl | C2H5 | H | CO | phenyl | 98 | 226–227 |
| 5 | 4-Cl-phenyl | CH3 | H | CO | 2-Cl-phenyl | 220 | 222–224 |
| 6 | 4-Cl-phenyl | CH3 | H | CO | 2-CF3-phenyl | 66 | 204–205 |
| 7 | phenyl | CH3 | H | CO | 2-F-phenyl | 96 | 162–164 |
| 8 | 4-Cl-phenyl | CH3 | H | CO | 2-OCH3-phenyl | 290 | 220–221 |
| 9 | 4-Br-phenyl | CH3 | H | CO | 2-pyridyl | >1000 | 238–239 |
| 10 | 4-NO2-phenyl | CH3 | H | CO | 2-Cl-phenyl | 310 | 217–219 |

-continued
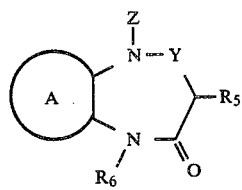
| No. | A | Z | R₅ | Y | R₆ | PAF-Antag. IC₅₀; [μMol] | Mp. °C. |
|---|---|---|---|---|---|---|---|
| 11 | 4-Cl-phenyl | CH₃ | H | CO | phenyl | 210 | 161–162 |
| 12 | 4-Br-phenyl | H | CH₃ | CO | phenyl | 350 | 316–318 |
| 13 | 4-Br-phenyl | CH₃ | H | CH₂ | phenyl | >1000 | 122–124 |
| 14 | 4-Cl-phenyl | (CH₂)₂—OH | H | CH₂ | phenyl | 285 | 153–157 |
| 15 | pyridyl | C₂H₅ | H | CH₂ | phenyl | >100 | 142–144 |
| 16 | pyridyl | CH₃ | H | CO | phenyl | >50 | 224–226 |
| 17 | 1-C₂H₅-3,5-(CH₃)₂-pyrazolyl | H | H | CO | phenyl | >100 | |
Compounds of formula:

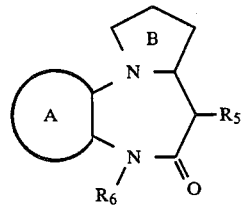

| No. | A | B | $R_5$ | $R_6$ | PAF-Antag. IC$_{50}$; [μMol] | Mp. °C. |
|---|---|---|---|---|---|---|
| 1 | 4-Cl-phenyl | 1-CH$_3$-5-CH$_3$-1,2,4-triazol-3-yl | H | phenyl | 16 | 292–294 |
| 2 | 4-Cl-phenyl | 1-CH$_3$-5-CH$_3$-1,2,4-triazol-3-yl | H | 2-CF$_3$-phenyl | 76 | 252–254 |
| 3 | 4-NO$_2$-phenyl | 1-CH$_3$-5-CH$_3$-1,2,4-triazol-3-yl | H | phenyl | 230 | 302–305 |
| 4 | 4-Cl-phenyl | 1-CH$_3$-5-CH$_3$-1,2,4-triazol-3-yl | H | 2-NO$_2$-phenyl | 450 | 288–290 |
| 5 | 4-Cl-phenyl | 4-CH$_3$-1,2,4-triazol-3-yl | H | 2-Br-phenyl | 360 | 315–318 |
| 6 | 4-Cl-phenyl | 1-CH$_3$-5-CH$_3$-1,2,4-triazol-3-yl | H | 2-Cl-phenyl | 240 | 278–280 |
| 7 | 4-Cl-phenyl | 5-Br-1-CH$_3$-1,2,4-triazol-3-yl | H | phenyl | 119 | 202–204 |
| 8 | 4-Cl-phenyl | 4-CH$_3$-1,2,4-triazol-3-yl | H | 2-Cl-phenyl | 520 | 280–282 |
| 9 | 1-C$_2$H$_5$-3,5-dimethylpyrazol-4-yl | 1-CH$_3$-5-CH$_3$-1,2,4-triazol-3-yl | H | phenyl | <200 | Oil |

-continued

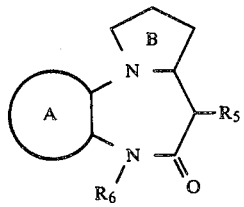

| No. | A | B | $R_5$ | $R_6$ | PAF-Antag. $IC_{50}$; [μMol] | Mp. °C. |
|---|---|---|---|---|---|---|
| 10 | 4-Br, 3-CH₃-phenyl | CH₃-triazolyl | H | phenyl | 554 | 282–284 |
| 11 | 4-NO₂, 3-CH₃-phenyl | triazolyl | H | phenyl | >1000 | 310–313 |
| 12 | 4-CF₃, 3-CH₃-phenyl | CH₃-triazolyl | H | phenyl | 280 | 266–268 |

The compounds of formula I and II can be administered to warm-blooded animals topically, orally, parenterally or by inhalation. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, emulsions, syrups, suppositories, etc. The effective dose range of the compounds according to the invention includes at least 10 to 500, preferably between 25 and 100 mg per dose for oral administration, and between 0.01 and 100, preferably between 0.1 and 50 mg per dose for intravenous or intramuscular application. Solutions containing 0.01 to 1.0, preferably 0.1 to 0.5% of active substance can be used for inhalation.

Some examples of pharmaceutical compositions will now be given in which compounds of formula I and II are used as the active ingredient.

Unless otherwise specifically stated, the parts given are parts by weight.

1. Tablets
The tablets include the following ingredients:

| | |
|---|---|
| Active substance of formula I and II | 0.050 parts |
| Stearic acid | 0.010 parts |
| Dextrose | 1.890 parts |
| Total | 1.950 parts |

Preparation:
The substances are mixed together in known manner and the mixture is compressed to form tablets, each of which weighs 1.95 g and contains 10 to 50 mg of active substance.

2. Ointment
The ointment includes of the following ingredients:

| | |
|---|---|
| Active substance of formula I and II | 2.000 parts |
| Sodium pyrosulphite | 0.050 parts |
| Mixture (1:1) of cetyl alcohol and stearyl alcohol | 20.000 parts |
| White Vaseline | 5.000 parts |
| Synthetic bergamot oil | 0.075 parts |
| Distilled water | ad 100.000 parts |

Preparation:
The ingredients are intimately mixed in known manner to form an ointment of which 100 g contain 2.0 g of the active substance.

3. Inhalation aerosol
The aerosol includes of the following ingredients:

| | |
|---|---|
| Active substance of formula I and II | 1.00 parts |
| Soya lecithin | 0.20 parts |
| Propellant gas mixture (Frigen ®) (11, 12, and 14) | ad 100.00 parts |

Preparation:
The ingredients are mixed together in a manner known per se and the mixture is transferred into aerosol containers which contain a metering valve releasing between 1 and 20 mg of active substance on each actuation.

4. Solution for ampoules
The solution includes of the following ingredients:

| | |
|---|---|
| Active substance of formula I and II | 5.0 parts |
| Polyethylene glycol | 400.0 parts |
| Benzyl alcohol | 15.0 parts |
| Ethyl alcohol (95%) | 100.0 parts |
| Sodium benzoate | 50.0 parts |
| Benzoic acid | 1.2 parts |

-continued

| Doubly distilled water | ad 1000.0 parts |

Preparation:

The active substance is dissolved in benzyl alcohol and then polyethylene glycol and alcohol are added. The sodium benzoate and benzoic acid are dissolved in 250 ml of water, combined with the above solution and made up to 1000 ml with water. The resulting solution is filtered free from pyrogens and the filtrate is transferred under aseptic conditions into 1 ml ampoules which are then sterilized and sealed by fusion. Each ampoule contains 1 to 5 mg of the active substance.

5. Suppositories

Each suppository includes:

| Active substance of formula I and II | 1.0 parts |
| Cocoa butter (m.p. 36–37° C.) | 1200.0 parts |
| Carnauba wax | 5.0 parts |

Preparation:

The cocoa butter and carnauba wax are melted together. At 45° C. the active substance is added and the mixture is stirred until a complete dispersion is formed. The mixture is poured into moulds of a suitable size and the suppositories are suitably packaged.

We claim:

1. A method of treating an individual having a disorder responsive to PAF-antagonist activity, which method comprises treating said individual with a therapeutically effective amount of a compound of formulae

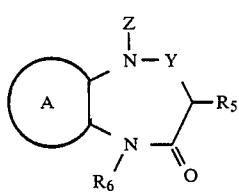

(I)

or

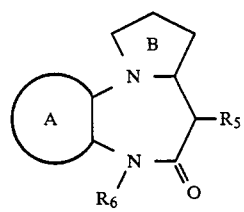

(II)

wherein

A is an anellated ring of formula

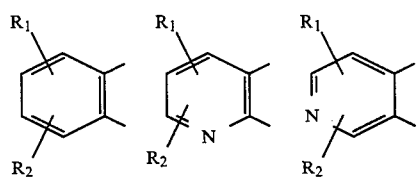

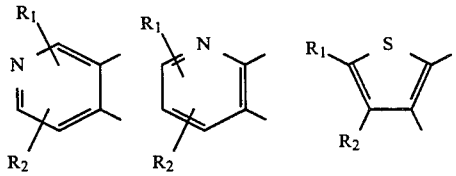

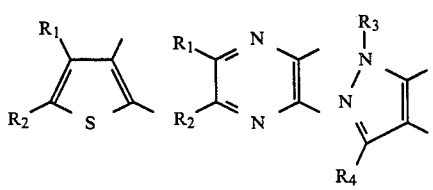

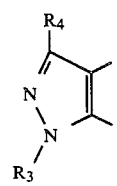

B is an anellated ring of formula

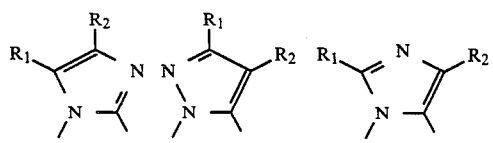

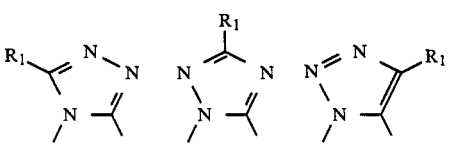

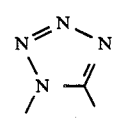

$R_1$ and $R_2$, are each independently hydrogen, a $C_1$–$C_8$ straight-chained or branched alkyl, alkenyl or alkynyl optionally mono- or polysubstituted by halogen, hydroxy, alkoxy, alkylmercapto, amino, alkylamino, dialkylamino, alkylcarbonyl, alkyloxycarbonyl or an acid amide group; cycloalkyl; a saturated carbocyclic or heterocyclic ring condensed on, which may contain oxygen, sulphur or nitrogen as a heteroatom while the nitrogen-containing ring can carry an alkyl group at the nitrogen atom; halogen, trifluoromethyl, nitro, cyano, optionally substituted amino, alkylmercapto, alkylcarbonyl, alkoxy, alkyloxycarbonyl or an acid amide group;

$R_3$, $R_4$ $R_5$ and Z are each independently hydrogen, a $C_1$–$C_8$ straight-chained or branched alkyl, alkenyl or alkynyl optionally mono- or polysubstituted by halogen, hydroxy, alkoxy, alkylmercapto, amino, alkylamino, dialkylamino, alkylcarbonyl, alkyloxycarbonyl, or an acid amide group;

$R_6$ is phenyl, which can optionally be substituted, preferably in the 2 position, by methyl, methoxy, halogen, nitro or trifluoromethyl, or R₆ can be thienyl or α-pyridyl;

Y is <CO, <CS or <CH₂; and non-toxic, pharmaceutically acceptable acid addition salts thereof.

2. The method of claim 1 which comprises treating with compounds of the formula

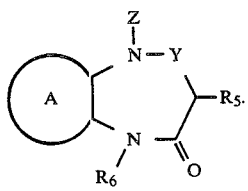

3. The method of claim 2 wherein Y is <CH₂
4. The method of claim 3 wherein Y is <CO
5. The method of claim 4 wherein
A is

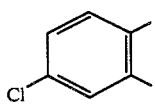

Z is C₂H₅
R₅ is hydrogen; and
Y is <CO
R₆ is

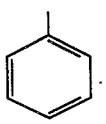

6. The method of claim 4 which comprises treating with compounds of the formula
A is

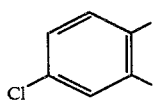

Z is CH₃
R₅ is hydrogen;
Y is <CO
R₆ is

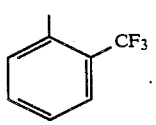

7. The method of claim 4 wherein
A is

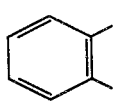

Z is CH₃

R₅ is H
Y is <CO and
R₆ is

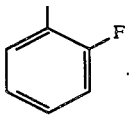

8. A method of claim 4 wherein
H is

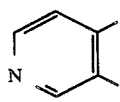

Z is CH₃
R₅ is H
Y is <CO
R₆ is

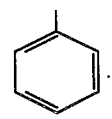

9. The method of claim 1 which comprises treating with compounds of the formula

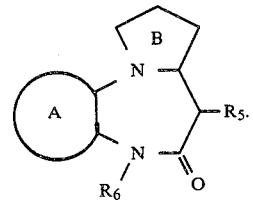

10. The method of claim 9 wherein
A is

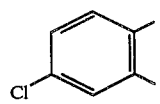

11. The method of claim 10 wherein
B is

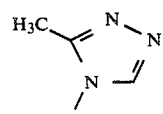

R₅ is H
R₆ is

12. B is
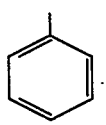
$R_5$ is H
$R_6$
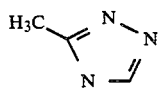
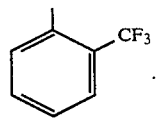
13. The method of claim 10 wherein B is
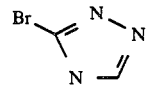
$R_5$ is H
$R_6$ is
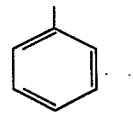
* * * * *